United States Patent

Motojima et al.

[11] Patent Number: 5,827,540
[45] Date of Patent: Oct. 27, 1998

[54] GRANULAR COMPOSITION WITH FUSED OR SLURRIED COATING

[75] Inventors: Shozo Motojima, Hadano; Masanori Serita; Yoko Watanabe, both of Kanagawa, all of Japan

[73] Assignee: Mitsubishi Chemical Corporation, Tokyo, Japan

[21] Appl. No.: 605,798

[22] Filed: Feb. 22, 1996

[30] Foreign Application Priority Data

Feb. 23, 1995 [JP] Japan .................................. 7-035627

[51] Int. Cl.$^6$ ...................................... A61K 9/14
[52] U.S. Cl. ..................... 424/489; 424/490; 424/405; 424/408
[58] Field of Search ................. 424/489, 490, 424/408, 405, 461, 1.29; 71/120; 47/12

[56] References Cited

U.S. PATENT DOCUMENTS

| 4,432,994 | 2/1984 | Giles et al. | 47/12 |
| 4,844,734 | 7/1989 | Iwasaki et al. | 71/120 |
| 5,120,542 | 6/1992 | Scher et al. | 424/405 |

*Primary Examiner*—Thurman K. Page
*Assistant Examiner*—William E. Benston, Jr.
*Attorney, Agent, or Firm*—Oblon, Spivak, McClelland, Maier & Neustadt, P.C.

[57] ABSTRACT

A granular composition consisting essentially of a granular carrier having a fused or slurried mixture comprising a pesticidally active ingredient, an antioxidant and/or an epoxy compound, and wax, coated thereon.

15 Claims, No Drawings

GRANULAR COMPOSITION WITH FUSED OR SLURRIED COATING

BACKGROUND OF THE INVENTION

1. Field of the Invention

The present invention relates to a granular composition containing an agricultural chemicals in a stabilized condition such as a granular pesticide or a granular fertilizer containing a pesticide.

2. Discussion of Background

A granular pesticide or a granular fertilizer having a pesticidal ingredient coated on a mineral granular carrier or on a granular fertilizer, is known. It is also known that in many cases, the carrier or fertilizer is strongly acidic or strongly alkaline, whereby the pesticidal ingredient is likely to be decomposed substantially and lose its effects in a short period of time. In an attempt to overcome such a problem, it has been proposed to mix a stabilizer to the pesticide or to coat the pesticidal ingredient with wax or oil before supporting it on the carrier or fertilizer (Japanese Unexamined Patent Publication No. 157493/1989).

However, satisfactory stabilizing effects have not necessarily been obtained.

SUMMARY OF THE INVENTION

It is an object of the present invention to provide a granular composition which contains a pesticidally active ingredient in a stabilized condition and which is widely applicable to pesticidally active ingredients, granular fertilizers and granular mineral matters which are commonly used.

Further, by application of such a granular composition, there will be effects for preventing e.g. pollution of rivers or the atmosphere. Especially when a granular fertilizer containing a pesticide is applied, it is possible to accomplish the effect of labor saving or rationalization of farming, as the operation for application of the fertilizer and the operation for application of the pesticide can thereby be done simultaneously.

The present inventors have conducted various studies to obtain a stabilized granular pesticide-containing fertilizer and a stabilized granular pesticide-containing mineral matter and have found that by coating a granular carrier with a fused or slurried mixture comprising a pesticidally active ingredient, and an antioxidant and/or an epoxy compound, it is possible to suppress decomposition of the pesticidally active ingredient and to maintain the pesticide in a stabilized condition even by a storage for a long period of time. The present invention has been accomplished on the basis of this discovery.

That is, the present invention provides a granular composition consisting essentially of a granular carrier having a fused or slurried mixture comprising a pesticidally active ingredient, an antioxidant and/or an epoxy compound, and wax, coated thereon.

DETAILED DESCRIPTION OF THE PREFERRED EMBODIMENTS

Now, the present invention will be described in detail with reference to the preferred embodiments.

In the present invention, the active ingredient is not particularly limited. However, an agricultural chemicals, especially a pesticide which is susceptible to decomposition in an acidic or alkaline condition, may, particularly suitably, be used. It includes, for example, organophosphorus pesticides such as diethyldichlorophenyl thiophosphate (liquid), 2-diethylamino-6-methylpyrimidine-4-isodimethylphosphorothioate (liquid), (2-isopropyl-4-methylpyrimidyl-6)-diethyl thiophosphate (liquid), o,o-diethyl-o-quinoxalin-2-yl-phosphorothioate (mp: 31°–32° C.), o,o-diethyl-o-(5-phenyl-3-isoxazolyl)phosphorothioate (liquid), o-4-bromo-2-chlorophenyl-o-ethyl-s-propyl-phosphorothioate (liquid), ethyl dimethyldithiophospholylphenyl acetate, o,o-dimethyl-s-(N-methylcarbamoylmethyl) dithiophosphate (liquid), o,o-dimethyl-s[5-methoxy-1,3,4-thiadiazole-2(3H)onyl-(3)-methyl] dithiophosphate (mp: 39°–40° C.), 3-(dimethoxyphosphinyloxy)-N-methyl-cis-crotonamide (mp:53°–54° C.), 2-chloro-1-(2,4-dichlorophenyl) vinyldimethyl phosphate (mp: 69°–70° C.), o,o-dipropyl-o-4-methylthiophenyl phosphate (liquid), ethyl p-nitrophenylthionobenzene phosphonate (mp: 36° C.), o,o-dimethyl=o-3-methyl-4-(methylsulfinyl)phenyl=phosphorothioate (mp: 57°–59° C.), (RS)-S-sec-butyl=o-ethyl=2-oxo-1,3-thiazolidine-3-ylphosphonothioate (liquid), o,o-dipropyl-s-benzylthiophosphate (mp: 23°–24° C.), o-ethyl-s,s-diphenyldithiophosphate (liquid), and S-(2-methyl-1-piperidyl-carbonylmethyl)-o,o-di-n-propyldithiophosphate; carbamate pesticides such as 2-isopropylphenyl-N-methylcarbamate (mp: 88°–93° C.), 2-secondary butylphenyl-N-methylcarbamate (mp: 31°–32° C.), 3,4-xylyl-N-methylcarbamate (mp: 71°–76° C.), 2,3-dihydro-2,2-dimethyl-7-benzo[b]furanyl=N-dibutylaminothio-N-methylcarbamate (liquid), ethyl=N-[2,3-dihydro-2,2-dimethylbenzofuran-7-yloxycarbonyl (methyl)aminothio]-N-isopropyl-β-alaninate (liquid), butyl-2,3-dihydro-2,2-dimethylbenzofuran-7-yl-N,N-dimethyl-N,N-thiodicarbamate (liquid), methyl-N',N'-dimethyl-N-[(methylcarbamoyl)oxy]-1-thiooxamimidate (mp: 108°–110° C.), and methyl-N-(3,4-dichlorophenyl)carbamate (mp: 42° C.); pyrethroid pesticides such as 5-benzyl-3-furylmethyldl-cis, trans-chrysanthemate (mp: 50° C.), (RS)-α-cyano-3-phenoxybenzyl-2,2,3,3-tetramethylcyclopropane carboxylate (mp: 50°–51° C.), (RS)-α-cyano-phenoxybenzyl=(RS)-2-(4-chlorophenyl)-3-methylbutanoate (liquid), and (RS)-α-cyano-3-phenoxybenzyl=N-(2-chloro-α,α,α-trifluoro-p-tolyl)-D-valinate (liquid); and other herbicides such as bisdimethyldithiocarbamoylzincethylenebis dithiocarbamate (grayish white powder), 1,3-bis(carbamoylthio)-2-(N,N-dimethylamino)propane (mp: 183°–186° C.), N-trichloromethylthiotetrahydro phthalimide (mp: 177°–178° C.), N-(p-fluorophenyl)-dichloromaleimide (mp: 244°–245° C.), 2,3-dicyano-1,4-dithiaanthraquinone (mp: 224°–225° C.), S-ethyl 2-methyl-4-chlorophenoxythioacetate (mp: 41°–42° C.), and a sodium salt of methyl 3-(1-allyloxyaminobutylidene)-6,6-dimethyl-2,4-dioxocyclohexane carboxylate (mp: 185° C.). In the present invention, such pesticidally active ingredients may be used alone or in combination as a mixture of two or more of them.

The antioxidant includes, for example, phenolic antioxidants such as 2,6-di-t-butyl-p-cresol (mp: 69° C.), butylated hydroxylanisole (mp: 57° C.), stearyl-β-(3,5-di-t-butyl-4-hydroxyphenyl) propionate (mp: 49°–52° C.), 2,2'-methylenebis(4-methyl-6-t-butylphenol) (mp: 120° C.), 2,2'-methylenebis(4-methyl-6-t-butylphenol) (mp: 119° C.), 4,4'-thiobis(3-methyl-6-t-butylphenol) (mp: 150° C.), 4,4'-butylidenebis(3-methyl-6-t-butylphenol) (mp: 205° C.), 1,1,3-tris(2-methyl-4-hydroxy-5-t-butylphenyl)butane (mp: 185°–188° C.), and tetrakis-[methylene-3-(3',5'-di-t-butyl-4'-phenyl)propionate]methane (mp: 120° C.); distearyl-3,3'- thiodipropionate (mp: 59° C., sulfur type); and triphenylphosphite (mp: 15° C., phosphorus type). However, phenolic antioxidants are preferred. In the present invention, such antioxidants may be used alone or in combination as a mixture of two or more of them.

The epoxy compound includes, for example, epoxidized vegetable oils such as epoxidized soybean oil and epoxidized linseed oil, glycidyl ethers such as cyclohexene oxide, epichlorohydrin and phenylglycidyl ether, and glycidyl esters such as coconut fatty acid glycidyl esters. However, epoxidized vegetable oils are preferred. In the present invention, such epoxy compounds may be used alone or in combination as a mixture of two or more of them.

The wax includes natural, synthetic and blend waxes. It includes, for example, candelilla wax (mp: 68°–72° C.), carnauba wax (mp: 80°–86° C.), beeswax (mp: 60°–67° C.), lanolin (mp: 37°–43° C.), montan wax (mp: 76°–82° C.), paraffin wax (mp: 45°–65° C.), olefin wax (mp: 75°–77° C.), polyethylene wax (grease wax) (vaseline-like), caster wax (mp: 85° C.), and stearic acid (mp: 58°–61° C.). In the present invention, such waxes may be used alone or in combination as a mixture of two or more of them.

The granular fertilizer to be used as a carrier is not particularly limited, and a wide range of granular fertilizers may be employed. It may, for example, be the one prepared by granulating a straight fertilizer such as urea, ammonium sulfate, calcium superphosphate, fused phosphate, potassium chloride or potassium sulfate, a quick-acting compound fertilizer such as a potassium sulfate/ammonium phosphate compound or a potassium sulfate/ammonium sulfate compound, or a compound fertilizer having a gradually acting fertilizer such as crotonylidene diurea, isobutylidenediurea or urea-form blended to such as straight fertilizer or quick-acting compound fertilizer. More specifically, a commercially available fertilizer such as "Kumiai Linster No. 30", manufactured by Mitsubishi Chemical Corporation, "Kumiai Urea-containing IB Kasei No. 042", manufactured by Mitsubishi Chemical Corporation, "Kumiai Super IB Compound S222", manufactured by Mitsubishi Chemical Corporation, "Kumiai potassium sulfate-ammonium phosphate No. 16", manufactured by Mitsubishi Chemical Corporation, "Kumiai potassium phosphate-ammonium phosphate compound No. 42", manufactured by Mitsubishi Chemical Corporation, "Kumiai urea-containing IB Kasei No. S1", manufactured by Ryohoku Kasei K.K., "Kumiai urea-containing potassium nitrogen Kasei No. 2", manufactured by Nippon Kasei K.K., or "Complex Berdy Turf", manufactured by Ryoto Hiryo K.K., is, for example, preferred.

In the present invention, such granular fertilizers may be used alone or in combination as a mixture of two or more of them.

The granular mineral matter is not particularly limited so long as it is a granular material commonly used as a carrier for agricultural chemicals. For example, it may be an inorganic carrier such as talc, bentonite, kaolin, clay or calcium carbonate. More specifically, a commercially available product such as "Galeonite #0248" (pH: 4.0, manufactured by Kanto Bentonite Kogyo K.K.), "Ishikawa Light No. 2" (pH: 4.0, manufactured by Asada Seifun K.K.), "Fine Granule No. 2" (pH: 8.5, manufactured by Asada Seifun K.K.), "Calcium Carbonate Granule" (pH: 10, manufactured by Kunimine Kogyo K.K.), or "Hojun Bentonite Granule" (pH: 10, manufactured by Hojun Yoko K.K.) is, for example, preferred. In the present invention, such granular mineral matters may be used alone or in combination as a mixture of two or more of them.

Further, to prevent caking, a powdery carrier such as diatomaceous earth, white carbon, talc or clay may preferably be incorporated to the surface of the granular composition. Further, to prevent floatation, a powdery surfactant such as "Sorpol 5050", manufactured by Toho Chemical Co., Ltd.) or sodium lignin sulfonate may, for example, be incorporated, as the case requires.

In the granular composition of the present invention, the pesticidally active ingredient is usually from 0.01 to 10% by weight, preferably from 0.1 to 5% by weight, based on the entire granular composition. Each of the antioxidant and the epoxy compound to be blended with the pesticidally active ingredient is usually in an amount of from 0.02 to 10% by weight, preferably from 0.3 to 5% by weight, based on the entire granular composition. Further, in a case where both the antioxidant and the epoxy compound are used in combination, the total amount is usually from 0.02 to 10% by weight, preferably from 0.3 to 5% by weight, based on the entire granular composition. Further, the wax is usually from 0.02 to 10% by weight, preferably from 0.3 to 5% by weight, based on the entire granular composition.

To prepare the granular composition of the present invention, the pesticidally active ingredient, the antioxidant and/or the epoxy compound, and the wax are heated and thoroughly mixed at a temperature at which the entire mixture will melt, and the fused or slurried mixture thereby obtained, is coated on a granular fertilizer or on a granular mineral matter to obtain the granular composition. In a case where the melting points of the pesticidally active ingredient, the antioxidant and the epoxy compound are higher than the melting point of the wax, the additives other than the wax are preliminarily finely pulverized and then mixed with the wax and the mixture is heated and thoroughly mixed at a temperature higher than the melting point of the wax, whereupon the obtained slurry is likewise coated on a granular fertilizer or on a granular mineral matter to obtain the granular composition of the present invention.

Further, instead of heat melting, a solvent may be used, so that the additives are coated on the carrier in the form of a solution or slurry, whereupon the solvent may be removed by e.g. heating.

More specifically, the coating method may be of a continuous system or of a batch system, and the apparatus may be any apparatus so long as sufficient rolling effects can be obtained. A rotation mixing drum, a tray type apparatus or one man mixer may, for example, be used.

With the granular composition of the present invention consisting essentially of a granular fertilizer or a granular mineral matter having a solution or slurry of a mixture comprising a pesticidally active ingredient, an antioxidant and/or an epoxy compound, and wax, coated thereon, it is evident, as shown by the following stability test results, that decomposition of the pesticidally active ingredient is distinctly prevented, as compared with granular compositions which do not belong to the present invention.

Now, the present invention will be described in further detail with reference to Examples. However, it should be understood that the present invention is by no means restricted to such specific Examples.

EXAMPLE 1

To 0.35 parts by weight of pesticidally active ingredient (RS)-S-sec-butyl=1-o-ethyl=2-oxo-1,3-thiazolidin-3-ylphosphonothioate (liquid, hereinafter referred to phosthiazate), 2.0 parts by weight of 2,6-di-t-butyl-p-cresol (mp: 69° C.) and 2.0 parts by weight of caster wax (mp: 85°

C.) were added and thoroughly stirred at 100° C. to obtain a uniform heat-melt mixture. On the other hand, in a jacketed small size pan, 95.65 parts by weight of "Kumiai potassium phosphate/ammonium phosphate compound No. 42" (granular compound fertilizer, manufactured by Mitsubishi Chemical Corporation) was warmed to a temperature of 45° C., and the above heat-melt mixture was gradually added thereto and coated thereon to obtain a granular pesticide-containing fertilizer.

EXAMPLE 2

To 0.35 part by weight of phosthiazate (liquid), 2.0 parts by weight of "Sorpol 7157" (liquid, epoxidized linseed oil, manufactured by Toho Chemical Co., Ltd.) and 2.0 parts by weight of caster wax (mp: 85° C.) were added and thoroughly stirred at 100° C. to obtain a uniform heat-melt mixture. This mixture was coated on 95.65 parts by weight of "Kumiai potassium phosphate/ammonium phosphate Compound No. 42" (granular compound fertilizer, manufactured by Mitsubishi Chemical Corporation) in the same manner as in Example 1 to obtain a granular pesticide-containing fertilizer.

EXAMPLE 3

To 0.35 part by weight of phosthiazate (liquid), 1.0 part by weight of 2,6-di-t-butyl-p-cresol (mp: 69° C.), 1.0 part by weight of "Sorpol 7157" (liquid, epoxidized bean seed oil, manufactured by Toho Chemical Co., Ltd.) and 2.0 parts by weight of caster wax (mp; 85° C.) were added and thoroughly stirred at 100° C. to obtain a uniform heat-melt mixture. This mixture was coated on 95.65 parts by weight of "Kumiai potassium phosphate/ammonium phosphate Compound No. 42" (granular compound fertilizer, manufactured by Mitsubishi Chemical Corporation) in the same manner as in Example 1 to obtain a granular pesticide-containing fertilizer.

EXAMPLE 4

To 0.35 part by weight of phosthiazate (liquid), 2.0 parts by weight of preliminarily thoroughly pulverized 2,6-di-t-butyl-p-cresol (mp: 69° C.) and 2.0 parts by weight of polyethylene wax (vaseline-like) were added and thoroughly stirred at 50° C. to obtain a uniform heat slurry product. This slurry product was coated on 95.65 parts by weight of "Kumiai potassium phosphate/ammonium phosphate Compound No. 42" (granular compound fertilizer, manufactured by Mitsubishi Chemical Corporation) in the same manner as in Example 1, followed by coagulation-preventing treatment with 1.0 part by weight of "Neocarrier M" (clay, manufactured by Asada Seifun K.K.) to obtain a granular pesticide-containing fertilizer.

EXAMPLE 5

To 0.35 part by weight of phosthiazate (liquid), 2.0 parts by weight of butylated hydroxylanisole (mp: 57° C.) and 2.0 parts by weight of "Dialen-30" (mp: 77° C., olefin wax, manufactured by Mitsubishi Chemical Corporation) were added and thoroughly stirred at 90° C. to obtain a uniform heat-melt mixture. This mixture was coated on 95.65 parts by weight of "Hojun Bentonite Granules" (pH: 10, bentonite granules, manufactured by Hojun Yoko K.K.) in the same manner as in Example 1 to obtain a granular pesticide-containing mineral matter.

EXAMPLE 6

To 0.35 part by weight of phosthiazate (liquid), 2.0 parts by weight of "Leoblast 39" (liquid, epoxidized soybean oil, manufactured by Hoechst) and 2.0 parts by weight of "Dialen-30" (mp: 77° C., olefin wax, manufactured by Mitsubishi Chemical Corporation) were added and thoroughly stirred at 90° C. to obtain a uniform heat-melt mixture. This mixture was coated on 95.65 parts by weight of "Hojun Bentonite Granules" (pH: 10, bentonite granules, manufactured by Hojun Yoko K.K.) in the same manner as in Example 1 to obtain a granular pesticide-containing mineral matter.

EXAMPLE 7

To 0.35 part by weight of phosthiazate (liquid), 1.0 part by weight of butylated hydroxyanisole (mp: 27° C.), 1.0 part by weight of "Leoblast 39" (liquid, epoxidized soybean oil, manufactured by Hoechst) and 2.0 parts by weight of "Dialen-30" (mp: 77° C., olefin wax, manufactured by Mitsubishi Chemical Corporation) were added and thoroughly stirred at 90° C. to obtain a uniform heat-melt mixture. This mixture was coated on 95.65 parts by weight of "Hojun Bentonite Grains" (pH: 10, bentonite granules, manufactured by Hojun Yoko K.K.) in the same manner as in Example 1 to obtain a granular pesticide-containing mineral matter.

EXAMPLE 8

To 0.35 part by weight of phosthiazate (liquid), 2.0 parts by weight of preliminarily thoroughly pulverized butylated hydroxyanisole (mp: 57° C.), 2.0 parts by weight of polyethylene wax (vaseline-like) were added and thoroughly stirred at 50° C. to obtain a uniform heat slurry product. This slurry product was coated on 95.65 parts by weight of "Hojun Bentonite Granules" (pH: 10, bentonite granules, manufactured by Hojun Yoko K.K.) in the same manner as in Example 1, followed by coagulation-preventing treatment with 1.0 part by weight of "Neocarrier M" (clay, manufactured by Asada Seifun K.K.) to obtain a granular pesticide-containing mineral matter.

EXAMPLE 9

To 1.0 part by weight of pesticidal ingredient 2-sec-butylphenyl-N-methylcarbamate (mp: 31°–32° C., hereinafter referred to as BPMC), 2.0 parts by weight of "Sorpol 7157" (liquid, epoxidized linseed oil, manufactured by Toho Chemical Co., Ltd.) and 2.0 parts by weight of "Dialen-30" (mp: 77° C., olefin wax, manufactured by Mitsubishi Chemical Corporation) were added and thoroughly stirred at 90° C. to obtain a uniform heat-melt mixture. This mixture was coated on 95.00 parts by weight of "Kumiai potassium sulfate/ammonium phosphate No. 16" (granular compound fertilizer, manufactured by Mitsubishi Chemical Corporation) in the same manner as in Example 1 to obtain a granular pesticide-containing fertilizer.

EXAMPLE 10

To 1.0 part by weight of preliminarily thoroughly pulverized pesticidally active ingredient 2-isopropylphenyl-N-methylcarbamate (mp: 88°–93° C., hereinafter referred to as MIPC), 2.0 parts by weight of butylated hydroxyanisole (mp: 57° C.) and 2.0 parts by weight of "Dialen-30" (mp: 77° C., olefin wax, manufactured by Mitsubishi Chemical Corporation) were added and thoroughly stirred at 85° C. to obtain a uniform heated slurry product. This slurry product was coated on 95.00 parts by weight of "Kumiai potassium sulfate/ammonium phosphate No. 16" (granular compound fertilizer, manufactured by Mitsubishi Chemical Corporation) in the same manner as in Example 1 to obtain a granular pesticide-containing fertilizer.

EXAMPLE 11

To 1.0 part by weight of pesticidal ingredient (RS)-α-cyano-3-phenoxybenzyl-N-(2-chloro-α,α,α-trifluoro-p-tolyl)-D-valinate (liquid, hereinafter referred to fluvalinate), 2.0 parts by weigh of "Leoblast 39" (liquid, epoxidized soybean oil, manufactured by Hoechst) and 2.0 parts by weight of "Dialen-30" (mp: 77° C., olefin wax, manufactured by Mitsubishi Chemical Corporation) were added and thoroughly stirred at 90° C. to obtain a uniform heat-melt mixture. This mixture was coated on 95.0 parts by weight of "Kumiai potassium sulfate/ammonium phosphate No. 16" (granular compound fertilizer, manufactured by Mitsubishi Chemical Corporation) in the same manner as in Example 1, to obtain a granular pesticide-containing fertilizer.

COMPARATIVE EXAMPLE 1

0.35 part by weight of phosthiazate (liquid) was preliminarily heated to 50° C. This was coated on 95.65 parts by weight of "Kumiai potassium phosphate/ammonium phosphate Compound No. 42" (granular compound fertilizer, manufactured by Mitsubishi Chemical Corporation), followed by coagulation-preventing treatment with 1.0 part by weight of "Neocarrier M" (clay, manufactured by Asada Seifun K.K.) to obtain a granular pesticide-containing fertilizer.

COMPARATIVE EXAMPLE 2

0.35 part by weight of phosthiazate (liquid) was preliminarily heated to 50° C. This was coated on 95.65 parts by weight of "Hojun Bentonite Granules" (pH: 10, bentonite granules, manufactured by Hojun Yoko K.K.) in the same manner as in Example 1, followed by coagulation-preventing treatment with 1.0 part by weight of "Neocarrier M" (clay, manufactured by Asada Seifun K.K.), to obtain a granular pesticide-containing mineral matter.

COMPARATIVE EXAMPLE 3

To 0.35 part by weight of phosthiazate (liquid), 2.0 parts by weight of caster wax (mp: 85° C.) was added and thoroughly stirred at 100° C. to obtain a uniform heat-melt mixture. This mixture was coated on 97.65 parts by weight of "Kumiai potassium phosphate/ammonium phosphate Compound No. 42" (granular compound fertilizer, manufactured by Mitsubishi Chemical Corporation) in the same manner as in Example 1 to obtain a granular pesticide-containing fertilizer.

COMPARATIVE EXAMPLE 4

To 0.35 part by weight of phosthiazate (liquid), 2.0 parts by weight of "Sorpol 7157" (liquid, epoxidized linseed oil, manufactured by Toho Chemical Co., Ltd.) was added, and the mixture was heated to 50° C. This mixture was coated on 96.65 parts by weight of "Kumiai potassium phosphate/ammonium phosphate Compound No. 42" (granular compound fertilizer, manufactured by Mitsubishi Chemical Corporation) in the same manner as in Example 1, followed by coagulation-preventing treatment with 1.0 part by weight of "Neocarrier M" (clay, manufactured by Asada Seifun K.K.) to obtain a pesticide-containing fertilizer.

COMPARATIVE EXAMPLE 5

1.0 part by weight of BPMC (mp: 31°–32° C.) was preliminarily heated to 50° C. This was coated on 98.00 parts by weight of "Kumiai potassium sulfate/ammonium phosphate No. 16" (granular compound fertilizer, manufactured by Mitsubishi Chemical Corporation) in the same manner as in Example 1, followed by coagulation-preventing treatment with 1.0 part by weight of "Neocarrier M" (clay, manufactured by Asada Seifun K.K.) to obtain a granular pesticide-containing fertilizer.

COMPARATIVE EXAMPLE 6

1.0 part by weight of machine oil was preliminarily added to 98.00 parts by weight of "Kumiai potassium sulfate/ammonium phosphate No. 16" (granular compound fertilizer, manufactured by Mitsubishi Chemical Corporation) to uniformly moisten the fertilizer. Then, 1.0 part by weight of thoroughly pulverized MIPC (mp: 88°–93° C.), was added thereto and uniformly coated to obtain a granular pesticide-containing fertilizer.

COMPARATIVE EXAMPLE 7

1.0 part by weight of fluvalinate (liquid) was preliminarily heated to 50° C. This was coated on 98.00 parts by weight of "Kumiai potassium sulfate/ammonium phosphate No. 16" (granular compound fertilizer, manufactured by Mitsubishi Chemical Corporation) in the same manner as in Example 1, followed by coagulation-preventing treatment with 1.0 part by weight of "Neocarrier M" (clay, manufactured by Asada Seifun K.K.) to obtain a granular pesticide-containing fertilizer.

EXAMPLE 12

To 1.0 part by weight of preliminarily thoroughly pulverized 1,3-bis(carbamoylthio)-2-(N,N-dimethylamino)propane hydrochloride (mp: 183°–186° C., hereinafter referred to as caltap), 2.0 parts by weight of butylated hydroxyanisole (mp: 57° C.), and 2.0 parts by weight of "Dialen-30" (mp: 77° C., olefin wax, manufactured by Mitsubishi Chemical Corporation), were added and thoroughly stirred at 90° C. to obtain a uniform heated slurry product. This slurry product was coated on 95.0 parts by weight of "Kumiai potassium sulfate/ammonium sulfate No. 16" (granular compound fertilizer, manufactured by Mitsubishi Chemical Corporation) in the same manner as in Example 1, to obtain a granular pesticide-containing fertilizer.

COMPARATIVE EXAMPLE 8

1.0 part by weight of machine oil was preliminarily added to 98.0 parts by weight of "Kumiai potassium sulfate/ammonium phosphate No. 16" (granular compound fertilizer, manufactured by Mitsubishi Chemical Corporation) to uniformly moisten the fertilizer. Then, 1.0 part by weight of thoroughly pulverized caltap (mp: 183°–186° C.), was added thereto and uniformly coated thereon to obtain a granular pesticide-containing fertilizer.

COMPARATIVE EXAMPLE 9

To 0.35 part by weight of phosthiazate (liquid), 2.0 parts by weight of butylated hydroxyanisole (mp: 57° C.), was added and thoroughly stirred at 80° C. to obtain a uniform heat-melt mixture. This mixture was coated on 97.65 parts by weight of "Kumiai potassium phosphate/ammonium phosphate Compound No. 42" (granular compound fertilizer, manufactured by Mitsubishi Chemical Corporation) in the same manner as in Example 1 to obtain a granular pesticide-containing fertilizer. By this method, a cotton-like powdery substance covered the surface of the fertilizer as the time passed, and dusting characteristics of the fertilizer deteriorated.

Stability Tests of the Pesticidally Active Ingredients

The granular pesticide-containing compositions improved by the present invention, as represented by Examples, and compositions of Comparative Examples were stored at a constant temperature of 40° C. for 30 days, 60 days and 90 days, whereupon the respective pesticidal ingredients were measured by HPLC, and the remaining ratios (%) relative to the initial contents of pesticidal ingredients were obtained and shown in Table 1.

TABLE 1

|  | Remaining ratios (%) | | |
| --- | --- | --- | --- |
|  | 40° C., 30 days later | 40° C., 60 days later | 40° C., 90 days later |
| Example 1 | 99.7 | 98.7 | 96.3 |
| Example 2 | 99.8 | 98.5 | 96.4 |
| Example 3 | 99.0 | 97.0 | 96.2 |
| Example 4 | 99.5 | 98.5 | 96.1 |
| Example 5 | 99.8 | 98.7 | 96.7 |
| Example 6 | 99.8 | 98.8 | 96.8 |
| Example 7 | 98.8 | 98.5 | 95.8 |
| Example 8 | 99.8 | 98.5 | 96.5 |
| Example 9 | 99.0 | 98.4 | 95.4 |
| Example 10 | 99.8 | 97.2 | 95.7 |
| Example 11 | 98.0 | 98.0 | 96.2 |
| Example 12 | 99.0 | 98.2 | 96.9 |
| Comparative Example 1 | 20.3 | 15.2 | 5.2 |
| Comparative Example 2 | 25.6 | 18.2 | 7.3 |
| Comparative Example 3 | 47.5 | 40.2 | 30.0 |
| Comparative Example 4 | 78.6 | 65.6 | 54.5 |
| Comparative Example 5 | 35.4 | 28.1 | 10.3 |
| Comparative Example 6 | 36.7 | 27.3 | 9.8 |
| Comparative Example 7 | 34.8 | 26.5 | 8.9 |
| Comparative Example 8 | 19.7 | 12.5 | 3.8 |
| Comparative Example 9 | 89.9 | 85.2 | 81.0 |

What is claimed is:

1. A granular composition, consisting essentially of a granular carrier having a fused or slurried mixture coated thereon, said coating comprising a pesticidally active ingredient, an antioxidant or an epoxy compound or both, and wax.

2. The granular composition according to claim 1, wherein the carrier is a granular fertilizer.

3. The granular composition according to claim 1, wherein the carrier is a granular mineral matter.

4. The granular composition according to claim 1, wherein the antioxidant is selected from the group consisting of phenolic antioxidants.

5. The granular composition according to claim 1, wherein the epoxy compound is selected from the group consisting of epoxidized vegetable oils.

6. The granular composition according to claim 1, wherein the pesticidally active ingredient is selected from the group consisting of organophosphorus pesticides.

7. The granular composition according to claim 1, wherein the pesticidally active ingredient is selected from the group consisting of carbamate pesticides.

8. The granular composition according to claim 1, wherein the pesticidally active ingredient is selected from the group consisting of pyrethroid pesticides.

9. The granular composition according to claim 1, wherein the pesticidally active ingredient is from 0.01 to 10% by weight based on the entire granular composition, the antioxidant and/or the epoxy compound is from 0.02 to 10% by weight based on the entire granular composition, and the wax is from 0.02 to 10% by weight based on the entire granular composition.

10. The granular composition according to claim 6, wherein said organophosphorous pesticide is selected from the group consisting of diethyldichlorophenyl thiophosphate, 2-diethylamino-6-methylpyrimidine-4-isodimethylphosphorothioate, (2-isopropyl-4-methylpyrimidino-6)-diethyl thiophosphate, o,o-diethyl-o-quinoxalin-2-yl-phosphorothioate, o,o-diethyl-o-(5-phenyl-3-isooxozolyl)phosphorothioate, o-4-bromo-2-chlorophenyl-o-ethyl-s-propylphosphorothioate, ethyl dimethyldithiophospholylphenyl acetate, o,o-dimethyl-s-(N-dimethylcarbamoylmethyl) dithiophosphate, o-o-dimethyl-s[5-methoxy-1,3,4-thiodiazole-2(3H)onyl-(3)-methyl] dithiophosphate, 3-(dimethoxyphosphinyloxy)-N-methyl-cis-crotonamide, 2-chloro-1-(2,4-dichlorophenyl) vinyldimethyl phosphate, o,o-dipropyl-o-4-methylthiophenyl phosphate, ethyl p-nitrophenolthionobenzene phosphonate, o,o-dimethyl-o-3-methyl-4-(methylsulfinyl)phenyl phosphorothioate (RS)-S-sec-butyl o-ethyl-2-oxo-1,3-thiazolidine-3-ylphosphonothioate, o,o-dipropyl-s-benzylthiphosphate, o-ethyl-s,s-diphenyldithiophosphate and S-(2-methyl-1-piperidyl-carbonylmethyl)-o,o-di-n-propyldithiophosphonate.

11. The granular composition according to claim 7, wherein said carbamate pesticide is 1,3-bis(carbamoylthiol)-2-(N,N-dimethylamino)propane.

12. The granular composition according to claim 4, wherein said phenolic antioxidant is selected from the group consisting of 2,6-di-t-butyl-p-cresol, butylated hydroxyanisole, stearyl-β-(3,5-di-t-butyl-r-hydroxyphenyl) propionate, 2,2'-methylenebis (4-methyl-6-t-butylphenol), 2,2'-methylenebis (4-methyl-6-t-butylphenol), 4,4'-thiobis (3-methyl-6-t-butylphenol), 4,4'-butylidenebis (3-methyl-6-t-butylphenol), 1,13-tris(2-methyl-4-hydroxy-5-t-butylphenyl)butane and tetrakis-[methylene-3(3',5'-di-t-butyl-4'-phenyl) propionate]methane.

13. The granular composition according to claim 5, wherein said epoxidized vegetable oil is selected from the group consisting of epoxidized soybean oil and linseed oil.

14. The granular composition according to claim 1, wherein said wax is selected from the group consisting of natural, synthetic and blend waxes.

15. The granular composition according to claim 14, wherein said wax is selected from the group consisting of candelilla wax, carnauba wax, beeswax, lanolin, martan wax, paraffin wax, olefin wax, polyethylene wax, caster wax and stearic acid.

* * * * *